(12) United States Patent
Jabalee

(10) Patent No.: US 6,817,991 B1
(45) Date of Patent: Nov. 16, 2004

(54) PROTECTIVE GARMENT AND METHOD FOR PREVENTING SPINAL INJURIES IN BABIES LEARNING TO WALK

(76) Inventor: Douglas Jabalee, P.O. Box 50174, Knoxville, TN (US) 37950

( * ) Notice: Subject to any disclaimer, the term of this patent is extended or adjusted under 35 U.S.C. 154(b) by 99 days.

(21) Appl. No.: 10/247,760

(22) Filed: Sep. 19, 2002

Related U.S. Application Data

(60) Provisional application No. 60/329,263, filed on Oct. 12, 2001, and provisional application No. 60/323,770, filed on Sep. 19, 2001.

(51) Int. Cl.[7] .................................................. A61F 13/15
(52) U.S. Cl. .............. 604/385.01; 604/369; 604/385.31
(58) Field of Search ....................... 604/385.01, 385.31, 604/385.16, 369; 2/466, 467, 2

(56) References Cited

U.S. PATENT DOCUMENTS

| | | | | | |
|---|---|---|---|---|---|
| 1,532,037 A | * | 3/1925 | Emett | ............................ | 2/463 |
| 2,621,327 A | * | 12/1952 | Amoroso | ........................ | 2/467 |
| 4,393,865 A | * | 7/1983 | Lambert | ....................... | 602/24 |
| 5,913,405 A | * | 6/1999 | Bordier | ......................... | 2/467 |

* cited by examiner

*Primary Examiner*—John J. Calvert
*Assistant Examiner*—Jacqueline Stephens
(74) *Attorney, Agent, or Firm*—John R. Benefiel

(57) ABSTRACT

A protective garment and method for preventing spinal injury in a child learning to walk in which an underpants garment is put on the child when walking, the garment cushioned in the lower seat area so as to substantially attenuate shock to the spine when the child suddenly sits down.

3 Claims, 1 Drawing Sheet

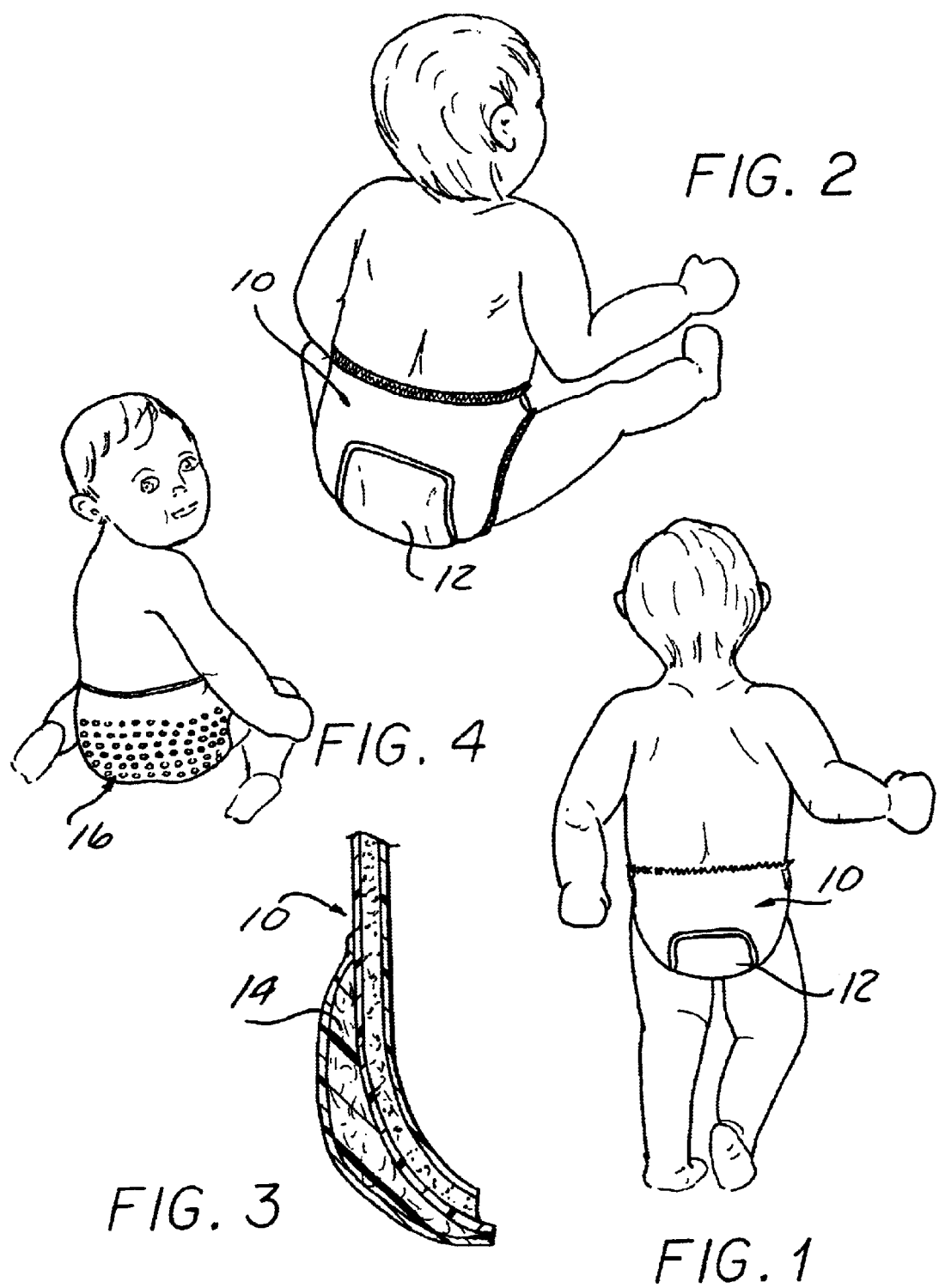

PROTECTIVE GARMENT AND METHOD FOR PREVENTING SPINAL INJURIES IN BABIES LEARNING TO WALK

CROSS REFERENCE TO RELATED APPLICATIONS

This application claims the benefit of U.S. provisional Ser. No. 60/329,263, filed Oct. 12, 2001 and 60/323,770 filed Sep. 19, 2001.

BACKGROUND OF THE INVENTION

This invention concerns protective garments to be worn by babies when first learning to walk.

It has been recognized that babies when first learning to walk often sit down abruptly when attempting to walk. It is believed that significant spinal damage is done when this happens, particularly in a child who repeats this many times over an extended period. Such injuries can have long lasting effects which only become apparent years later.

Cushioning of diapers has been provided in the past to hold the thighs in an abducted position, as shown in U.S. Pat. No. 4,964,858.

Diaper cushioning has also been provided to prevent excessive skin pressure such as described in U.S. Pat. No. 5,868,725.

Neither of these are designed to be worn to protect the child from the spinal injuries described above when learning to walk.

It is the object of the present invention to provide a protective garment and method for preventing such injuries in babies when they are learning to walk.

SUMMARY OF THE INVENTION

The above object and others which will be understood upon a reading of the following specification and claims are achieved by providing an underpants type garment, which could be comprised of a diaper, configured to allow normal leg positioning to allow the infant to walk, which is cushioned in a location in the garment seat beneath the wearer's bottom so as to protect the lower end of the child's spine when the baby suddenly drops down into a seated position, by substantially attenuating the shock to the spine. The cushion can be affixed to the exterior of a diaper, with a suitable cushioning material such as a compressible soft foam, an air cell, bubble wrap, creped tissue, etc.

DESCRIPTION OF THE DRAWINGS

FIG. 1 is a rear view of an erect toddler wearing a protective garment according to the invention.

FIG. 2 is a rear view of the toddler wearing the protective garment in the seated position.

FIG. 3 is a fragmentary sectional view of the garment portion illustrating the outer cushion patch according to the invention.

FIG. 4 is a rear view of a toddler wearing another embodiment of the protective garment according to the invention.

DETAILED DESCRIPTION

In the following detailed description, certain specific terminology will be employed for the sake of clarity and a particular embodiment described in accordance with the requirements of 35 USC 112, but it is to be understood that the same is not intended to be limiting and should not be so construed inasmuch as the invention is capable of taking many forms and variations within the scope of the appended claims.

Referring to FIG. 1, a walking toddler is shown wearing a protective garment 10, which comprises an underpants type garment 10 having a cushioning 12 disposed over the rear seat area extending down sufficiently far to absorb the shock to the spine when the baby drops to the seated position shown in FIG. 2. The garment 10 is configured to allow normal movement of the wearer's legs during walking.

The cushioning 12 may take the form of an external patch enclosing a volume 14 of cushioning material, such as an elastomeric foam pad, an air cell, a bubble sheet, layers of creped or stacked tissue paper. Such cushioning should be sufficiently thick and shock absorbent to substantially attenuate the shock imposed on the spine when the infant suddenly drops to the seated position.

The cushioning material may be applied by an external patch secured to an otherwise conventional disposable diaper as shown in FIGS. 1 and 2.

Alternatively, a bubble wrap complete sheath can be worn over a conventional diaper or underpants as shown in FIG. 4.

This protective garment will protect the relatively fragile body of the infant, particularly the spine when put on the baby during the period when the baby still has an unsteady gait and evidences a tendency to suddenly drop to the seated position.

I claim:

1. A protective garment for an infant comprised of a disposable diaper adapted to be worn by the child having a cushioning integrally attached thereto located over a seat portion, said cushioning configured and located to substantially attenuate the shock which otherwise would be imposed on the lower end of the infant's spine when the infant abruptly drops to the seated position.

2. The protective garment according to claim 1 wherein said cushioning comprises a patch attached to the outside of the diaper in the lower seat area thereof.

3. The protective garment according to claim 1 wherein said cushioning comprises a bubble wrap layer integrated into said diaper.

* * * * *